United States Patent [19]

Heywang et al.

[11] Patent Number: 4,778,511

[45] Date of Patent: Oct. 18, 1988

[54] FLUORINE-CONTAINING N-SULPHENYLATED INDAZOLES FOR USE AS BACTERICIDES AND FUNGICIDES

[75] Inventors: Gerhard Heywang, Bergisch Gladbach; Bernd Baasner; Albrecht Marhold, both of Leverkusen; Wilfried Paulus, Krefeld; Paul Reinecke; Hans-Georg Schmitt, both of Leverkusen, all of Fed. Rep. of Germany

[73] Assignee: Bayer Aktiengesellschaft, Leverkusen, Fed. Rep. of Germany

[21] Appl. No.: 830,593

[22] Filed: Feb. 18, 1986

[30] Foreign Application Priority Data

Feb. 21, 1985 [DE] Fed. Rep. of Germany ....... 3505905

[51] Int. Cl.$^4$ .................. C07D 231/56; C07D 471/00; C07D 239/00; C07D 487/00
[52] U.S. Cl. ........................................ 71/67; 514/243; 514/403; 514/293; 514/395; 514/257; 548/372; 546/82; 544/251; 544/184
[58] Field of Search ............... 514/403, 293, 395, 257, 514/243; 546/82; 548/372; 544/251, 184; 71/67

[56] References Cited

U.S. PATENT DOCUMENTS

| | | | |
|---|---|---|---|
| 3,647,818 | 3/1972 | Fenyes | 548/372 |
| 3,786,152 | 1/1974 | Minieri | 548/372 |
| 3,867,540 | 2/1975 | Fenyes | 548/372 |

FOREIGN PATENT DOCUMENTS 1568790  5/1969  France ................. 548/372

Primary Examiner—John M. Ford
Assistant Examiner—Robert C. Whittenbaugh
Attorney, Agent, or Firm—Sprung Horn Kramer & Woods

[57] ABSTRACT

Novel fluorine-containing N-sulfenylated indazoles are prepared by reacting the corresponding indazoles with sulfenyl halides in the presence of a solvent and/or diluent and in the presence of an acid-binder. The novel fluorine-containing N-sulfenylated indazoles are useful in the protection of industrial materials against attack by microorganisms such as bacteria, fungi, yeast, algae, and slime as plant protection agents, and in combating insects and arachrids.

9 Claims, No Drawings

FLUORINE-CONTAINING N-SULPHENYLATED INDAZOLES FOR USE AS BACTERICIDES AND FUNGICIDES

The present invention relates to new, fluorine-containing N-sulphenylated indazoles, a process for their preparation and their use in the production of materials and as a plant protection agent.

It is already known that certain N-sulphenylated indazoles have fungicidal and microbicidal properties (see U.S. Pat. No. 3,867,540). However, in certain fields of indication, particularly at low application rates and concentrations, the action of these compounds is not always satisfactory.

New flourine-containing N-sulphenylated indazoles of the general formula (I)

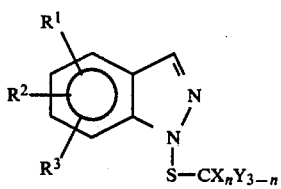

wherein
X and Y represent hydrogen,
n denotes 0, 1, 2 or 3 and
$R^1$, $R^2$ and $R^3$ are identical or different and represent halogen, a nitro group, an optionally monosubstituted or polysubstituted alkyl, alkoxy or alkylthio group or represent an opotionally monosubstituted or polysubstituted fused ring which is optionally interrupted by heteroatoms, and, if $R^1$, $R^2$ or $R^3$ represent halogen or a nitro group, one or more of the other substituents mentioned must always be present in addition, and at least one of the radicals $R^1$ to $R^3$ represents fluorine and/or at least one of the radicals $R^1$ to $R^3$ contains a fluorine-substituted carbon atom, have now been found.

Halogens in the formula (I) which may be mentioned are: fluorine, chlorine and bromine, preferably fluorine and chlorine; alkyl groups which may be mentioned are those having 1 to 6, preferably 1 to 4, carbon atoms, such as methyl, ethyl, n-propyl, isopropyl, n-butyl, isobutyl, sec.-butyl, tert.-butyl and pentyl, preferably methyl, ethyl, n-propyl and isopropyl; alkoxy groups which may be mentioned are those having 1 to 4, preferably 1 to 2 carbon atoms, such as methoxy, ethoxy and propoxy, preferably methoxy and ethoxy, and alkylthio groups which may be mentioned are those having 1 to 4, preferably 1 to 2 carbon atoms, such as methylthio, ethylthio and propylthio, preferably methylthio and ethylthio.

The radicals $R^1$, $R^2$ and $R^3$ in the formula (I) can also represent a fused ring, preferably a 5-membered or 6-membered ring, which is interrupted one or more times by oxygen, sulphur or nitrogen, preferably by 1 or 2 oxygen or sulphur atoms, and which can be substituted by fluorine, chlorine or bromine.

Examples of suitable substituents in the above-mentioned alkyl, alkoxy and alkylthio groups are: fluorine, chlorine and bromine, preferably fluorine and chlorine.

Preferred new fluorine-containing N-sulphenylated indazoles are those of the formula (II)

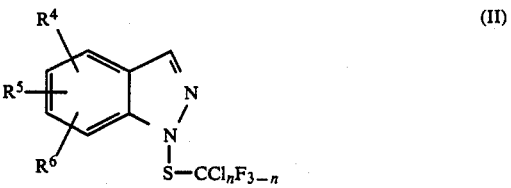

wherein
n denotes 0, 1, 2 or 3 and
$R^4$, $R^5$ and $R^6$ are identical or diffferent and represent fluorine, chlorine, bromine, a nitro group or a methyl, ethyl, methoxy, ethoxy, propoxy, methylthio or ethylthio group which is optionally substituted by fluorine, chlorine or bromine, or represents a fused 5-membered or 6-membered ring which is optionally monosubstituted or polysubstituted by fluorine or chlorine and is interrupted by 1 or 2 oxygen atoms, and, if $R^4$, $R^5$ and $R^6$ represent fluorine, chlorine, bromine or nitro, one or more of the other substituents mentioned must always be present in addition, and at least one of the radicals $R^4$ to $R^6$ represents fluorine and/or at least one of the radicals $R^4$ to $R^6$ contains a fluorine-substituted carbon atom.

New fluorine-containing N-sulphenylated indazoles which are particularly preferred are those of the formula (III)

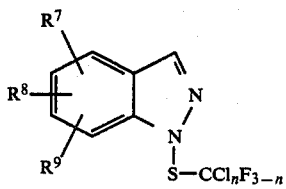

wherein
n denotes 0, 1, 2 or 3 and
$R^7$, $R^8$ and $R^9$ are identical or different and represent methyl, fluoromethyl, difluoromethyl, trifluoromethyl, chloromethyl, dichloromethyl, trichloromethyl, chlorodifluoromethyl, difluoromethyl, methoxy, fluoromethoxy, difluoromethoxy, trifluoromethoxy, chlorodifluoromethoxy, dichlorofluoromethoxy, 1,1,2,2-tetrafluoroethoxy, 2-chloro-1,1,2-trifluoroethoxy, 2,2,2-trifluoroethoxy, 2,2-dichloro-1,1,2-trifluoroethoxy, 2-chloro-1,1,2,2-tetrafluoroethoxy, 2-chloro-2,2-difluoroethoxy, 2,2-dichloro-2-fluoroethoxy, 2,2,2-trichloroethoxy, 1,1,2,3,3,3-hexafluoropropoxy, methylthio, chlorodifluoromethylthio, difluoromethylthio, trifluoromethylthio, 5,6-dioxomethylene, 5,6-dioxodifluoromethylene, 5,6-dioxo-chlorofluoromethylene, 5,6-dioxo-ethylene, 5,6-dioxo-difluoroethylene, 5,6-dioxo-trifluoroethylene, 5,6-dioxo-tetrafluoroethylene, 5,6-dioxo-chlorotrifluoroethylene, 5,6-dioxo-dichlorodifluoroethylene, 5,6-dioxo-chlorodifluoroethylene, 5,6-dioxo-chlorofluoroethylene or 5,6-dioxo-dichlorofluoroethylene.

The following new fluorine-containing N-sulphenylated indazoles may be mentioned particularly as examples: 1-trichloromethylsulphenyl-4-trifluoromethoxyindazole, 1-trichloromethylsulphenyl-5-trifluoromethoxyindazole, 1-trichloromethylsulphenyl-6-trifluoromethoxyindazole, 1-dichlorofluoromethylsulphenyl-4-trifluoromethoxyindazole, 1-dichlorofluoromethylsulphenyl-5-trifluoromethoxyindazole, 1- dichlorofluoromethylsulphenyl-6-trifluoromethoxyindazole, 1-trifluoromethylsulphenyl-4-trifluoromethoxyindazole, 1-trifluoromethylsulphenyl-5-trifluoromethoxyindazole, 1-trifluoromethylsulphenyl-6-trifluoromethoxyindazole, 1-dichlorofluoromethylsulphenyl-4-trifluoromethyl-6-methyl-7-chloroindazole, 1-dichlorofluoromethylsulphenyl-5-difluoromethoxyindazole, 1-dichlorofluoromethylsulphenyl-[2-chloro-1,1,2-trifluoroethoxy]-indazole, 1-dichlorofluoromethylsulphenyl-5-chlorodifluoromethoxyindazole, 1-dichlorofluoromethylsulphenyl-4-chloro-5-trifluoromethoxyindazole, 1-dichlorofluoromethylsulphenyl-4-methyl-5-trifluoromethoxyindazole, 1-dichlorofluoromethylsulphenyl-5-bromo-6-fluoroindazole, 1-dichlorofluoromethylsulphenyl-5,7-dimethyl-6-trifluoromethylindazole, 1-dichlorofluoromethylsulphenyl-6-trifluoromethylthioindazole, 1-dichlorofluoromethylsulphenyl-4,5-dichloro-6-trifluoromethylindazole, 1-dichlorofluoromethylsulphenyl-5-dichlorofluoromethylthioindazole, 1dichlorofluoromethylsulphenyl-5-trifluoromethylthioindazole, 1-dichlorofluoromethylsulphenyl-6-dichlorofluoromethylthioindazole, 1-dichlorofluoromethylsulphenyl-6-difluoromethoxyindazole, 1-dichlorofluoromethylsulphenyl-5-trifluoromethyl-6-chlorindazole, 1-dichlorofluoromethylsulphenyl-5-trifluoromethyl-6-fluoroindazole, 1-dichlorofluoromethylsulphenyl-4-trifluoromethyl-6-chloroindazole, 1-dichlorofluoromethylsulphenyl-5-(2,2,2-trifluoroethoxy)-indazole, 1-dichlorofluoromethylsulphenyl-5-(1,1,2,2-tetrafluoroethoxy)-indazole, 1-dichlorofluoromethylsulphenyl-6-(1,1,2,2-tetrafluoroethoxy)-indazole, 1-dichlorofluoromethylsulphenyl-6-(2,2,2-trifluoroethoxy)-indazole, 1-dichlorofluoromethylsulphenyl-4-methyl-6-fluoroindazole and 1-dichlorofluoromethylsulphenyl-6,7-dichloro-4-trifluoromethyl-indazole.

The invention also relates to a process for the preparation of the new fluorine-containing N-sulphenylated indazoles.

Accordingly, a process has been found for the preparation of the new fluorine-containing N-sulphenylated indazoles of the formula (I)

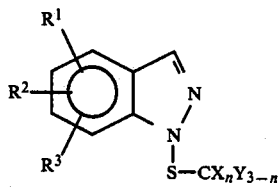

wherein

X and Y represent halogen, n denotes 0, 1, 2 or 3 and $R^1$, $R^2$ and $R^3$ are identical or different and represent halogen, a nitro group, an optionally monosubstituted or polysubstituted alkyl, alkoxy or alkylthio group or represent an optionally monosubstituted or polysubstituted fused ring which is optionally interrupted by heteroatoms, and, if $R^1$, $R^2$ or $R^3$ represent halogen or a nitro group, one or more of the other substituents mentioned must always be present in addition, and at least one of the radicals $R^1$ to $R^3$ represents fluorine and/or at least one of the radicals $R^1$ to $R^3$ contains a fluorine-substituted carbon atom, which is characterised in that indazoles of the formula (V)

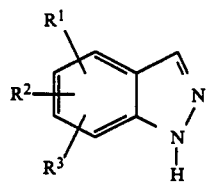

wherein $R^1$, $R^2$ and $R^3$ are identical or different and have the abovementioned meaning, are reacted, in the presence of a solvent and/or diluent and in the presence of an acid-binding agent, with sulphenyl halides of the formula (VI)

$$Z—S—CX_nY_{3-n} \qquad (VI)$$

wherein

X, Y and n have the above meaning and

Z represents halogen, preferably chlorine or bromine.

If, for example, 5-trifluoromethoxyindazole is reacted with dichlorofluoromethanesulphenyl chloride, the course of the reaction of the process according to the invention can be represented by the following equation:

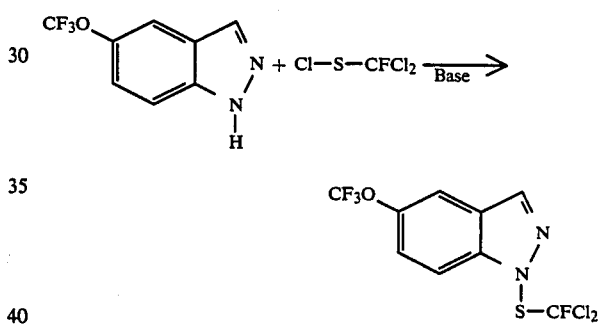

The indazoles of the formula (V) which are employed as starting materials in carrying out the process according to the invention are in part new. They can be prepared by known processes, for example by reacting the corresponding o-toluidines with an alkyl nitrite and/or nitrous gases (see, for example, DE-OS (German Published Specification) No. 2,155,545 and U.S. Pat. No. 3,988,347).

The o-toluidines required for the preparation of the indazoles of the formula (V) to be employed are also new in part and can be prepared by known processes by nitrating the corresponding toluenes with, for example, nitration acid, and subsequent reduction with hydrogen in the presence of a catalyst, such as Raney nickel or palladium, if appropriate on active charcoal (see, for example, DE-OS (German Published Specification) Nos. 3,023,328 and 3,135,926).

Solvents or diluents suitable for the process according to the invention are, in particular: aromatic hydrocarbons, such as benzene and/or toluene; halogenated hydrocarbons, such as methylene chloride and/or carbon tetrachloride; nitriles, such as acetonitrile and/or propionitrile; ethers, such as tetrahydrofuran and/or dioxane; and esters, such as ethyl acetate.

Acid-binding agents which can be employed for the process according to the invention are all customary organic and inorganic acid-binding agents. These preferably include tertiary amines, such as triethylamine or pyridine; and alkali metal hydroxides and/or alkali metal carbonates, such as sodium hydroxide and/or potassium hydroxide and sodium bicarbonate and/or potassium carbonate.

In carrying out the process according to the invention, the reaction temperatures can be varied within a fairly large range. In general, the reaction is carried out at temperatures of about 0° to 150° C., preferably at 20° to 100° C.

The indazoles of the formula (V) and the sulphenyl halides of the formula (VI) are preferably employed in equimolar amounts in the process according to the invention. Per mole of indazole it is preferable to employ about 0.8 to 3, particularly preferentially 0.85 to 1.5, moles of sulphenyl halide.

The new N-sulphenylated indazoles of the general formula (I) are isolated in a manner which is generally customary, for example by adding water to the reaction mixture, extracting the latter with an organic solvent and chromatography or distillation.

The new fluorine-containing N-sulphenylated indazoles, in particular the N-trihalogenomethylthioindazoles, are distinguished by a broad and powerful microbicidal action which also embraces algae and slime organisms. The substances according to the invention are therefore excellently suitable for protecting industrial materials.

In accordance with the invention, industrial materials are non-living materials which have been prepared for use in industry. Examples of industrial materials which are intended to be protected against microbial change or destruction by means of active compounds according to the invention can be adhesives, glues, paper and cardboard, textiles, leather, wood, paints and plastic articles, coolant-lubricants and other materials which can be attacked or decomposed by microorganisms. Sections of production facilities, for example cooling water circuits, which can be impaired by the propagation of micro-organisms may also be mentioned in relation to the materials to be protected. Industrial materials which may be mentioned within the scope of the present invention are preferably adhesives, glues, paper and cardboard, leather, wood, paints, coolant-lubricants and cooling circuits.

Bacteria, fungi, yeasts, algae and slime organisms may be mentioned as examples of microorganisms which can cause degradation or change in industrial materials. The active compounds according to the invention are preferentially effective against fungi, in particular mould fungi and fungi which discolour and destroy wood (Basidiomycetes), and against slime organisms and algae.

Microorganisms of the following genera may be mentioned as examples: Alternaria, such as *Alternaria tenuis,* Aspergillus, such as *Aspergillus niger,* Chaetomium, such as *Chaetomium globosum,* Coniophora, such as *Coniophora puteana,* Lentinus, such as *Lentinus tigrinus,* Penicillium, such as *Penicillium glaucum,* Polyporus, such as *Polyporus versicolor,* Aureobasidium, such as *Aureobasidium pullulans,* Sclerophoma, such as *Sclerophoma pityophila,* Trichoderma, such as *Trichoderma viride,* Escherichia, such as *Escherichia coli,* Pseudomonas, such as *Pseudomonas aeruginosa* and Staphylococcus, such as *Staphylococcus aureus.*

Depending on the field of application, an active compound according to the invention can be converted into the customary formulations, such as solutions, emulsions, suspensions, powders, pastes and granules.

These can be prepared in a manner which is in itself known, for example by mixing the active compounds with a diluent consisting of a liquid solvent and/or solid carriers, if appropriate with the use of surface-active agents, such as emulsifiers and/or dispersing agents, it being possible to use organic solvents, such as alcohols, as auxiliaries if required, in the event that water is used as the diluent.

Examples of liquid solvents for the active compounds can be water, alcohols, such as lower aliphatic alcohols, preferably ethanol or isopropanol, or benzyl alcohol, ketones, such as acetone or methyl ethyl ketone, liquid hydrocarbons, such as petroleum fractions, or halogenated hydrocarbons, such as 1,2-dichloroethane.

The active compounds are generally present in microbicidal agents in an amount of 1 to 95%, preferably 10 to 75%.

The concentrations at which the active compounds according to the invention are used depend on the nature and occurrence of the microorganisms to be combated, and also on the composition of the material to be protected. The optimum amount to be employed can be determined by test series. In general, the concentrations of use are within the range from 0.001 to 5% by weight, preferably from 0.05 to 1.0% by weight, relative to the material to be protected.

The active compounds according to the invention can also be in the form of a mixture with other known active compounds. The following active compounds may be mentioned as examples: benzyl alcohol mono(poly)hemiformal, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, organo-tin compounds, methylene bisthiocyanate, 2-thiocyanomethylthiobenzothiazole and phenol derivatives, such as 2-phenylphenol, (2,2'-dihydroxy-5,5'-dichloro)-diphenylmethane and 3-methyl-4-chlorophenol.

The fluorine-containing N-sulphenylated indazoles according to the invention are also suitable for use in plant protection agents.

By virtue of their fungicidal action they can be employed in plant protection for combating Plasmodiophoromycetes, Oomycetes, Chytridiomycetes, Zygomycetes, Ascomycetes, Basidiomycetes and Deuteromycetes.

By virtue of their bactericidal action, the active compounds according to the invention can be employed in plant protection for combating Pseudomonadaceae, Rhizobiaceae, Enterobacteriaceae, Corynebacteriaceae and Streptomycetaceae.

The good toleration by plants of the active compounds in the concentrations required for combating plant diseases makes it possible to treat parts of plants above ground, plants and seed and the soil.

In addition, the indazoles according to the invention are suitable for combating animal pests, in particular insects and arachnids, which occur in agriculture, in forests, in the protection of provisions and materials and in the hygiene sector.

EXAMPLES

Preparation examples

Example 1

6-Trifluoromethoxy-1-trichloromethylsulphenylindazole 18.6 g (0.1 mole) of trichlorosulphenyl chloride, dissolved in 125 ml of toluene, are added dropwise, in the course of one hour and at 80° to 85° C., to 20.2 g (0.1 mole) of 6-trifluoromethoxyindazole and 10.1 to (0.1 mole) of triethylamine in 125 ml of toluene. The mixture is stirred for a further hour at the same temperature. After cooling, the precipitated triethylamine hydrochloride is filtered off with suction and rinsed with toluene. The filtrate, combined with the wash liquor, is washed twice with water. After drying (MgSO$_4$), the volatile constituents are removed by distillation under a water pump vacuum; the residue crystallises after a little time and is purified by pressing on clay. Melting point 45° C. Yield 23 g (77% of theory).

Example 2

6-Trifluoromethoxy-1-dichlorofluoromethylsulphenylindazole 16.9 g (0.1 mole) of fluorodichloromethylsulphenyl chloride, dissolved in 125 ml of toluene, are added dropwise, in the course of one hour and at 80° to 85° C., to 20.2 g (0.1 mole) of 6-trifluoromethoxyindazole and 10.1 g (0.1 mole) of triethylamine in 125 ml of toluene. The mixture is stirred for a further hour at the same temperature. After cooling, the precipitated triethylamine hydrochloride is filtered off with suction and rinsed with toluene. The filtrate, combined with the wash liquor, is washed twice with water. After drying (MgSO$_4$), the volatile constituents are removed by distillation under a water pump vacuum. The oily residue is purified by distillation under a high vacuum. Boiling point 100° C./0.4 mbar. Yield: 17.1 g (51% theory).

Example 3

6-Trifluoromethoxy-1-trifluoromethylsulphenylindazole 20.2 g (0.1 mole) of 6-trifluoromethoxyindazole and 10.1 g (0.1 mole) of triethylamine in 125 ml of toluene are heated to 80° to 85° C., and 13.6 g (0.1 mole) of trifluoromethanesulphenyl chloride are then passed in the course of one hour and the mixture is stirred for a further hour at this temperature. After cooling, the precipitated triethylamine hydrochloride is filtered off with suction and rinsed with toluene. The filtrate, combined with the wash liquor, is washed twice with water. After drying (MgSO$_4$) the volatile constituents are removed by distillation under a water pump vacuum. The oily crude product is purified by distillation under an oil pump vacuum. Boiling point 62°/0.05 mbar. Yield: 16.2 g (46% of theory).

The compounds listed in the table below were prepared analogously. In some cases the compounds were purified by chromatography over silica gel using toluene as the mobile phase.

| Example No. | Compound | Melting point (°C.) | Boiling point (°C./mbar) | Yield (%) |
| --- | --- | --- | --- | --- |
| 4 | (structure: difluoromethylenedioxy-indazole with S—CFCl$_2$) | | 150/0.5 | 41 |
| 5 | CF$_3$O-indazole with S—CFCl$_2$ | | 110/0.3 | 75 |
| 6 | F$_3$CO-indazole with S—CCl$_3$ | $n_D^{20}$: 1.5408, Oil | | 92 |
| 7 | F$_3$CO-indazole with S—CF$_3$ | $n_D^{20}$: 1.4515, Oil | | 55 |
| 8 | CF$_3$/CH$_3$/Cl-indazole with S—CFCl$_2$ | M.P. 53–55 | | 84 |

-continued

| Example No. | Compound | Melting point (°C.) | Boiling point (°C./mbar) | Yield (%) |
|---|---|---|---|---|
| 9 | F₂HCO—[benzindazole]—N—S—CFCl₂ | Oil, n_D²⁰: 1.5810 | | 46,5 |
| 10 | Cl—CF(H)—CF₂—O—[benzindazole]—N—S—CFCl₂ | | B.p. 148–152/0.3 | 71 |
| 11 | Cl—CF₂—O—[benzindazole]—N—S—CFCl₂ | | B.p. 176–180/0.4 | 69 |
| 12 | CF₃O, Cl substituted [benzindazole]—N—S—CFCl₂ | | Oil n_D²⁰: 1.543 | 75 |
| 13 | F, CH₃ substituted [benzindazole]—N—S—CFCl₂ | 120 | | 57 |
| 14 | Br, F substituted [benzindazole]—N—S—CFCl₂ | 72–74 | | 72 |
| 15 | CH₃, CF₃, CH₃ substituted [benzindazole]—N—S—CFCl₂ | | Oil n_D²⁰: 1.5492 | 58 |
| 16 | CF₃S substituted [benzindazole]—N—S—CFCl₂ | | Oil n_D²⁰: 1.5602 | 85 |
| 17 | Cl, Cl, CF₃ substituted [benzindazole]—N—S—CFCl₂ | 90 | | 88 |

-continued

| Example No. | Compound | Melting point (°C.) | Boiling point (°C./mbar) | Yield (%) |
|---|---|---|---|---|
| 18 | CF$_3$S-[indazole]-N-S-CFCl$_2$ | 54 | | 94 |
| 19 | CH$_3$, F-substituted indazole-N-S-CFCl$_2$ | | Oil $n_D^{20}$: 1.5730 | 78 |
| 20 | F$_3$C-[indazole]-N-SCFCl$_2$ | 42 | | 93 |
| 20a | CF$_3$, Cl, Cl-substituted indazole-N-S-CCl$_2$F | 51 | | 71 |

Use examples

Example 20

The minimum inhibitory concentrations (MIC) of active compounds according to the invention are determined in order to demonstrate their effectiveness against fungi:

Active compounds, according to the invention, are added in concentrations of 0.1 mg/l to 5000 mg/l, to an agar prepared from beer wort and peptone. After the agar has solidified, it is contaminated with pure cultures of the test organisms listed in the table. The MIC is determined after the agar has been stored for 2 weeks at 28° C. and 60 to 70% relative atmospheric humidity. MIC is the lowest concentration of active compound at which the species of microbe used undergoes no growth at all; it is shown in the table below.

Example 21

A mixed culture of green, blue and brown algae and diatoms (*Stichococcus bacillaris* Naegeli, *Euglena gracilis* Klebs, *Chlorella pyrenoidosa* Chick, *Phormidium foveolarum* Gomont, *Oscillatoria geminata* Meneghini and *Phaeodactylum tricornutum* Bohlin) is introduced, by bubbling air through, into Allen's nutrient solution (Arch. Mikrobiol. 17, 34 to 53 (1952)), containing 0.2 g of ammonium chloride, 4.0 g of sodium nitrate, 1.0 g of dipotassium hydrogenphosphate, 0.2 g of calcium chloride, 2.05 g of magnesium sulphate and 0.02 g of iron chloride in 4 l of sterile water. After 2 weeks the nutrient solution has turned a deep green-blue colour as a result of intensive growth of algae. Decolorisation of the nutrient solution after active compounds according to the invention have been added indicates that the algae have been killed.

TABLE 1

MIC in mg/l when substances according to the invention act on fungi

| Test organisms | 2 | 4 | 8 | 12 | 1 | 15 | 16 | 5 | 17 | 18 | 19 | Additional comparison test 1-Dichlorofluoromethylsulphenyl-4-fluoroindazole* |
|---|---|---|---|---|---|---|---|---|---|---|---|---|
| *Alternaria tenuis* | 75 | | | 200 | 150 | | | 20 | | | 15 | |
| *Aspergillus niger* | 20 | 150 | 500 | 50 | 20 | 50 | <20 | 20 | 500 | <20 | 10 | 500 |
| *Aureobasidium pullulans* | 150 | | | 500 | 350 | | | 20 | | | 50 | |
| *Chaetomium globosum* | 2 | 100 | <20 | 20 | 75 | <20 | <20 | 20 | <20 | <20 | 10 | 200 |
| *Cladosporium* | 20 | | | 20 | 20 | | | | | | 5 | |
| *Lentinus tigrinus* | 20 | | | 7.5 | 75 | | | 0.1 | | | 0.5 | |
| *Penicillium glaucum* | 2 | 100 | <20 | 20 | 20 | <20 | <20 | 20 | <20 | <20 | 20 | 200 |
| *Polyporus versicolor* | | | | | | | | 2 | | | | |
| *Sclerophoma pityophila* | 35 | | | 200 | 75 | | | 0.75 | | | 15 | |
| *Trichoderma viride* | | | | | | | | 50 | | | 500 | |

*(in accordance with Claim 1 of U.S. Pat. No. 3,867,540)

TABLE 2

| Algae-destroying concentrations (mg/l) of the substance indicated below | |
| --- | --- |
| Active compound | Destructive concentration, mg/l |
| Compound from Example No. 5 | 50 |

Example 22

(action against slime organisms)

Substances according to the invention are used in concentrations of 0.1 to 100 mg/l in each case, dissolved in a little acetone, in Allen's nutrient solution (Arch. Mikrobiol. 17, 34 to 53 (1952)) containing 0.2 g of ammonium chloride, 4.0 g of sodium nitrate, 1.0 g of dipotassium hydrogenphosphate, 0.2 g of calcium chloride, 2.05 g of magnesium sulphate and 0.02 g of iron chloride, together with 1% of caprolactam, in 4 l of sterile water. Shortly beforehand, the nutrient solution is infested with slime organisms (approx. $10^6$ microbes/ml), isolated from the spinning water circulation used in the production of polyamide. Nutrient solutions containing the minimum inhibitory concentration (MIC) or higher concentrations of active compound are still completely clear after being cultured at room temperature for 3 weeks, that is to say the vigorous propagation of the microbes and formation of slime which is noticeable after 3 to 4 days in nutrient solutions free from active compound does not occur.

TABLE 3

| MIC values in mg/l when the substance indicated below acts on slime organisms | |
| --- | --- |
| Active compound | MIC/mg/l |
| Compound from Example No. 5 | 5-10 |

Example 23

Drechslera graminea test (barley)/seed treatment (syn. Helminthosporium gramineum)

The active compounds are applied in the form of dry dressing agents. They are formulated by diluting the particular active compound with ground minerals to give a finely powdered mixture, which ensures uniform distribution on the surface of the seed.

The infested seed is dressed by shaking it for 3 minutes with the dressing agent in a closed glass jar.

Embedded in sieved, moist standard soil, the seed is exposed to a temperature of 4° C. for 10 days in closed Petri dishes in a refrigerator. This initiates the germination of the barley sand, if appropriate, also that of the fungus spores. The pre-germinated barley is then sown in 2 lots of 50 grains 3 cm deep in standard soil and is cultivated in seed boxes which are exposed to light for 15 hours a day in a greenhouse at a temperature of approx. 18° C.

The plants are evaluated for symptoms of stripe disease approx. 3 weeks after sowing.

TABLE

| Drechslera graminea test (barley)/seed treatment (syn. Helminthosporium gramineum) | | |
| --- | --- | --- |
| Active compound | Application rate of active compound, mg/kg of seed | Diseased plants as % of all the emerged pants |
| undressed | — | 23.4 |
| known: | | |
| $CH_2-NH-CS-S$<br>$\phantom{CH_2-NH-CS-S}$Zn (Zineb)<br>$CH_2-NH-CS-S$ | 500 | 18.0 |
| in accordance with the invention: | | |
| Compound from Example No. 2 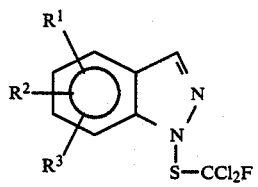 | 500 | 4.1 |

What is claimed is:

1. A fluorine containing N-sulfenylated indazole

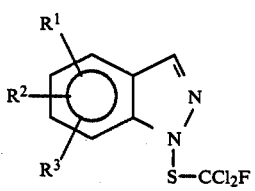

wherein $R^1$, $R^2$ and $R^3$ are identical or different and represents hydrogen, halogen, an optionally monosubstituted or polysubstituted alkyl, having 1 to 6 carbon atoms, alkoxy having 1 to 4 carbon atoms or alkylthio group having 1 to 4 carbon atoms, wherein the substituents are selected from the group consisting of fluorine, chloride and bromine or represent an optionally monosubstituted or polysubstituted 5,6-methylenedioxy or 5,6-ethylenedioxy and wherein the substituents are selected from the group consisting of fluorine, bromine and chlorine, and, if $R^1$, $R^2$ or $R^3$ represent halogen, one or more of the other substituents mentioned must always be present in addition, and at least one of the radicals $R^1$ to $R^3$ represents fluorine or contains a fluorine-substituted carbon atom.

2. A microbicidal agent effective against bacteria, fungi, yeasts, algae and slime organisms comprising, as the active compound, a fluorine-containing N-sulfenylated indazole of the formula wherein $R^1$, $R^2$ and $R^3$ are identical or different and represent hydrogen halogen, an optionally monosubstituted or polysubstituted alkyl, having 1 to 6 carbon atoms, alkoxy having 1 to 4 carbon atoms or alkylthio group having 1 to 4 carbon atoms, wherein the substituents are selected from the group consisting of fluorine, chlorine and bromine or represent an optionally monosubstituted or polysubstituted 5,6-methylenedioxy or 5,6-ethylenedioxy and wherein the substituents are selected from the group consisting of fluorine, bromine and chlorine, and, if $R^1$, $R^2$ or $R^3$ represent halogen, one or more of the other substituents mentioned must always be present in addition, and at least one of the radicals $R^1$ to $R^3$ represents fluorine or contains a fluorine-substituted carbon atom.

3. A microbicidal agent according to claim 2, comprising 1 to 95% of the active compound.

4. A method of protecting an industrial material against microbial change and destruction by bacteria, fungi, yeasts, algae and slime organisms comprising applying to said material a microbiocidally effective amount of the microbiocidal agent of claim 2.

5. A method according to claim 4 wherein 0.001 to 5% by weight of the active compound relative to said material is employed.

6. A method of protecting a plant from attack by microorganisms selected from the group consisting of bacteria, fungi, yeasts and slime organisms comprising applying to said plant a microbiocidally effective amount of the microbiocidal agent according to claim 4.

7. A fluorine-containing N-sulfenylated indazole according to claim 1 of the formula

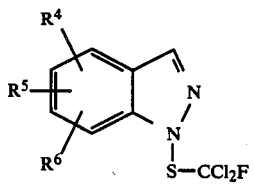

wherein
$R^4$, $R^5$ and $R^6$ are identical or different and represent hydrogen fluorine, chlorine, bromine, or a methyl, ethyl, methoxy, ethoxy, propoxy, methylthio or ethylthio group which is optionally substituted by fluorine, chlorine or bromine, or represents 5,6-methylenedioxy or 5,6-ethylenedioxy which is optionally monosubstituted or polysubstituted by fluorine or chlorine and, if $R^4$, $R^5$ and $R^6$ represents fluorine, chlorine, or bromine, one or more of the other substituents mentioned must always be present in addition, and at least one of the radicals $R^4$ to $R^6$ contains a fluorine-substituted carbon atom.

8. A fluorine-containing N-sulfenylated indazole according to claim 1 of the formula

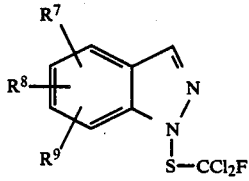

wherein
$R^7$, $R^8$ and $R^9$ are identical or different and represent hydrogen methyl, fluoromethyl, difluoromethyl, trifluoromethyl, chloromethyl, dichloromethyl, trichloromethyl, chlorodifluoromethyl, difluoromethyl, methoxy, fluoromethoxy, difluoromethoxy, trifluoromethoxy, chlorodifluoromethoxy, dichlorofluoromethoxy, 1,1,2,2-tetrafluoroethoxy, 2-chloro-1,1,2-trifluoroethoxy, 2,2,2-trifluoroethoxy, 2,2-dichloro-1,1,2-trifluoroethoxy, 2-chloro-1,1,2,2-tetrafluoroethoxy, 2-chloro-2,2-difluoroethoxy, 2,2-dichloro-2-fluoroethoxy, 2,2,2-trichloroethoxy, 1,1,2,3,3,3-hexafluoropropoxy, methylthio, chlorodifluoromethylthio, difluoromethylthio, trifluoromethylthio, 5,6-methylenedioxy, 5,6-difluoromethylenedioxy, 5,6-chlorofluoromethylenedioxy, 5,6-ethylenedioxy, 5,6-difluoroethylenedioxy, 5,6-trifluoroethylenedioxy, 5,6-tetrafluoroethylenedioxy, 5,6-chlorotrifluoroethylenedioxy, 5,6-dichlorodifluoroethylenedioxy, 5,6-chlorodifluoroethylenedioxy, 5,6-chlorofluoroethylenedioxy or 5,6-dichlorofluoroethylenedioxy.

9. A fluorine-containing N-sulfenylated indazole according to claim 1 selected from the group consisting of [1-trichloromethylsulfenyl-4-trifluoromethoxyindazole, 1-trichloromethylsulfenyl-5-trifluoromethoxyindazole, 1-trichloromethylsulfenyl-6-trifluoromethoxyindazole,] 1-dichlorofluoromethylsulfenyl-4-trifluoromethoxyindazole, 1-dichlorofluoromethylsulfenyl-5-trifluoromethoxyindazole, 1-dichlorofluoromethylsulfenyl-6-trifluoromethoxyindazole, [1-trifluoromethylsulfenyl-4-trifluoromethoxyindazole, 1-trifluoromethylsulfenyl-5-trifluoromethoxyindazole, 1-trifluoromethylsulfenyl-6-trifluoromethoxyindazole,] 1-dichlorofluoromethylsulfenyl-4-trifluoromethyl-6-methyl-7-chloroindazole, 1-dichlorofluoromethylsulfenyl-5-difluoromethoxyindazole, 1-dichlorofluoromethylsulfenyl-[2-chloro-1,1,2-trifluoroethoxy]-indazole, 1-dichlorofluoromethylsulfenyl-5-chlorodifluoromethoxyindazole, 1-dichlorofluoromethylsulfenyl-4-chloro-5-trifluoromethoxyindazole, 1-dichlorofluoromethylsulfenyl-4-methyl-5-trifluoromethoxyindazole, 1-dichlorofluoromethylsulfenyl-5-bromo-6-fluoroindazole, 1-dichlorofluoromethylsulfenyl-5,7-dimethyl-6-trifluoromethylindazole, 1-dichlorofluoromethylsulfenyl-6-trifluoromethylthioindazole, 1-dichlorofluoromethylsulfenyl-4,5-dichloro-6-trifluoromethylindazole, 1-dichlorofluoromethylsulfenyl-5-dichlorofluoromethylthioindazole, 1-dichlorofluoromethylsulfenyl-5-trifluoromethylthioindazole, 1-dichlorofluoromethylsulfenyl-6-dichlorofluoromethylthioindazole, 1-dichlorofluoromethylsulfenyl-6-difluoromethoxyindazole, 1-dichlorofluoromethylsulfenyl-5-trifluoromethyl-6-chloroindazole, 1-dichlorofluoromethylsulfenyl-5-trifluoromethyl-6-fluoroindazole, 1-dichlorofluoromethylsulfenyl-4-trifluoromethyl-6-chloroindazole, 1-dichlorofluoromethylsulfenyl-5-(2,2,2-trifluoroethoxy)-indazole, 1-dichlorofluoromethylsulfenyl-5-(1,1,2,2-tetrafluoroethoxy)-indazole, 1-dichlorofluoromethylsulfenyl-6-(1,1,2,2-tetrafluoroethoxy)-indazole, 1-dichlorofluoromethylsulfenyl-6-(2,2,2-trifluoroethoxy)-indazole, 1-dichlorofluoromethylsulfenyl-4-methyl-6-fluoroindazole and 1-dichlorofluoromethylsulfenyl-6,7-dichloro-4-trifluoromethyl-indazole.

* * * * *